United States Patent [19]

Nelson

[11] 4,438,767
[45] Mar. 27, 1984

[54] EXFOLIATOR DISC

[76] Inventor: Priscilla E. Nelson, 11 Brentwood Dr., Peabody, Mass. 01960

[21] Appl. No.: 956,260

[22] Filed: Oct. 30, 1978

[51] Int. Cl.³ .............................................. A61B 17/00
[52] U.S. Cl. .................................... 128/304; 128/355; 30/169
[58] Field of Search ........................ 128/304, 355, 757; D24/28; 15/236 R, 236 A; 30/169, 136; 17/16, 19

[56] References Cited

U.S. PATENT DOCUMENTS

| | | | |
|---|---|---|---|
| 604,965 | 5/1898 | Cartwright | 30/169 X |
| 1,538,521 | 5/1925 | Sheridan | 30/169 |
| 2,380,855 | 7/1945 | Lower | 30/169 X |
| 3,516,159 | 6/1970 | Bercier | 30/169 |
| 4,017,970 | 4/1977 | Williams | 30/169 |

*Primary Examiner*—Michael H. Thaler

[57] ABSTRACT

A flat circular blade is provided including opposite side finger tip engageable grip portions generally centered relative to the blade with the peripheral edge of the blade being laterally deflected to define a scraping edge for scraping dead skin tissue from various areas of the body.

2 Claims, 4 Drawing Figures

EXFOLIATOR DISC

BACKGROUND OF THE INVENTION

Various forms of devices have been heretofore provided for scraping outer skin areas. However, most of these previously known forms of scrapers have been provided with scraping edges primarily for use with cleansing creams or as massage devices.

Examples of various forms of previously known scrapers are disclosed in U.S. Pat. Nos. 1,683,410, 1,965,861, 2,380,855, 2,437,316 and 3,133,301.

BRIEF DESCRIPTION OF THE INVENTION

The exfoliator disc of the invention is a circular flat scraper that has been specifically designed in a manner enabling a scraping edge to be safely utilized for the purpose of scraping skin tissue.

The scraper is substantially circular in configuration and the scraping edge of the blade is placed against the skin in inclined relation thereto so that movement of the scraper will effectively scrape away dead skin tissue, cells and the like on various body areas.

An object of this invention is to provide a scraper which may be utilized by persons having acne or dry aging skin lines.

Another object of this invention to be specifically enumerated herein is to provide a skin scraper in accordance with the preceding object and which will conform to conventional forms of manufacture, be of simple construction and easy to use so as to provide a device that will be economically feasible, long lasting and trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
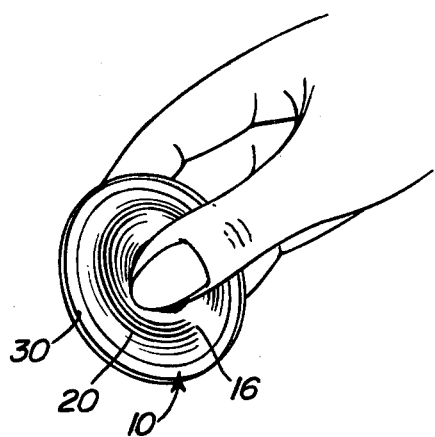
FIG. 1 is a perspective view illustrating the manner in which the scraper may be held between the thumb and fingers of one hand of the user.
Figure 2:
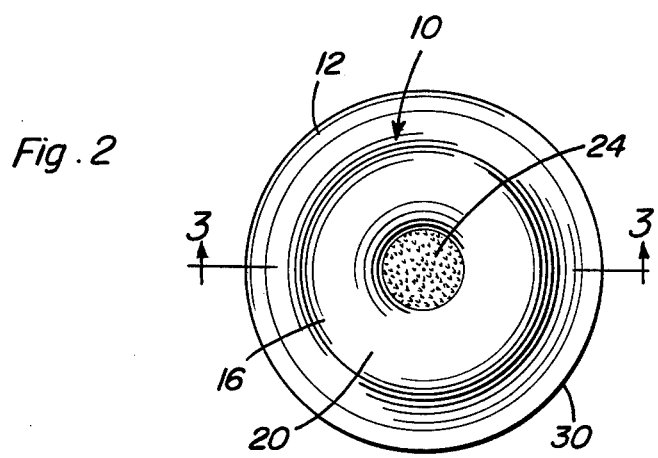
FIG. 2 is a plan view of the scraper.
Figure 3:
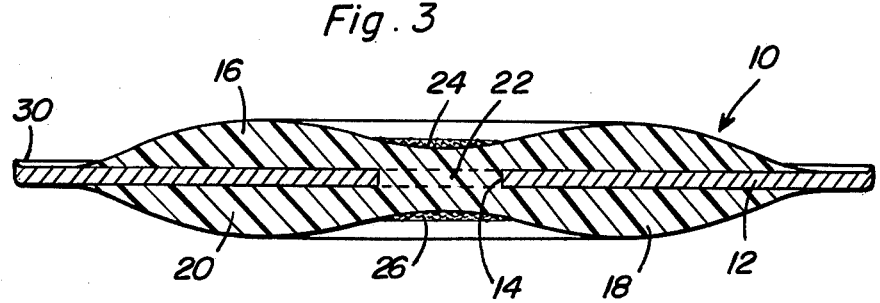
FIG. 3 is an enlarged transverse vertical sectional view taken substantially upon the plane indicated by the section line 3—3 of FIG. 2.

Referring now more specifically to the drawings, the numeral 10 generally designates the exfoliator disc of the instant invention which is in the form of a circular scraper which includes a circular flat blade 12 having a central aperture 14 formed therethrough. Opposite side integral portions 16 and 18 of a one-piece finger grip 20 overlie opposite side portions of the blade 12 and a central portion 22 of the finger grip 20 extends through the aperture 14 and connects the portions 16 and 18. It is to be noted that the finger grip 20 is molded to the blade 12 in a single molding process and that the opposite side portions 16 and 18 include central roughened recesses 24 and 26 to afford a non-slip grip of the finger grip 20 between the thumb and fingers of the user's hand.

Figure 4:
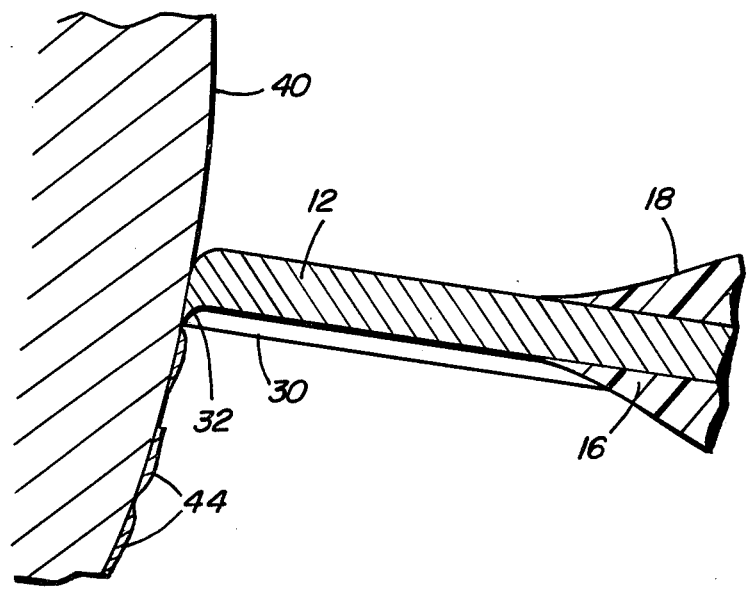
FIG. 4 is an enlarged fragmentary vertical sectional view illustrating the manner in which the scraper edge on the outer periphery of the scraper may be advanced to remove dead skin tissue.

The blade 12 is circular in plan shape and is, preferably, formed by a punching or stamping operation whereby the plate 12 may be cut from a larger plate of the same material, such as conventional sheet metal. During the punching or stamping operation, a deflected edge 30 is formed about the outer circular perihery of the blade 12 with the edge 30 projecting laterally of the side of the blade on which the finger grip portion 16 is disposed. The edge 30 is cupped as at 32, thus defining an effective scraping edge. The scraping edge also has a lateral dimension in the same direction as the lateral deflection of the scraping edge which is substantially less than the thickness of the blade as illustrated in FIG. 4. Further, FIG. 4 illustrates the minute radial dimension of the deflected edge 30 as measured along the radius of the disc as well as the deflected edge 30 tapering laterally to a feather edge with the peripheral side of the deflected edge forming with the peripheral edge of the blade a cylindrical surface.

In operation, the scraper is held between the thumb and fingers in a manner such as that illustrated in FIG. 1 of the drawings and may be positioned with the peripheral edge of the blade 12 engaged with the face or other skin area 40 to be scraped in the manner illustrated in FIG. 4 of the drawings. Thereafter, the scraper may be advanced in any direction in order to scrape dead skin portions 44 from the area 40.

If the user of the scraper has reason to believe that the skin area 40 to be scraped may be subject to excessive scraping action by the edge 32 when the scraper is held in the position illustrated in FIG. 4 because of irregular skin surfaces, the scraper may be inclined relative to the skin area 40 so as to vary the angular relation between the scraper and the skin area 40 thereby varying the scraping action. Thus, by constructing the scraper with the scraping edge 32 facing laterally, the scraping action of the edge 32 on the skin area 40 may be controlled.

This invention will effectively improve skin condition by mild dermabrasion which removes dead skin tissue or cells which can cause blocked pores. It can be used on all areas of the body with the thin circular disc being easy to maneuver and control. The flat construction of the disc allows the material scraped from the skin to be collected on the disc during use and easily rinsed off with water. The disc is easily cleaned and dried to facilitate the disc being retained in bacteria-free condition. Use of the exfoliator disc will facilitate draining and cleaning of clogged pores to allow healing from beneath the skin, reduce or eliminate surface scars from acne, reduce or dry excess oil in pores, stimulate blood circulation, reduces or eliminates fine age lines and exposes new moist skin tissue and generally invigorates the skin and improves complexion.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An exfoliator disc for scraping and removing dead skin tissues comprising a thin, flat, circular metal blade, opposite side finger tip engageable grip portions generally centered relative to the blade, the peripheral edge of the blade including a continuous, laterially deflected scraping edge projecting laterally to only one side of said blade, said blade having a constant thickness and parallel flat surfaces extending to the deflected edge, said deflected scraping edge being formed when the blade is sheared from stock metal and having a lateral dimension in the same direction as the lateral deflection of the scraping edge that is substantially less than the thickness of the blade and a minute radial dimension measured along the radius of the disc, said deflected edge also tapering laterally to a feather edge with the peripheral side of the deflected edge forming with the peripheral edge of the blade a cylindrical surface.

2. The combination of claim 1 wherein said grip portions define shallow oppositely outwardly imperforate opening finger tip receiving recesses, said blade including a center aperture extending therethrough, said grip portions being formed integrally with a connecting portion thereof extending through said aperture.

* * * * *